United States Patent [19]

Ericsson et al.

[11] Patent Number: 5,759,404
[45] Date of Patent: Jun. 2, 1998

[54] METHOD FOR SEPARATION AND SYNTHETIC POLYMERS THAT CAN BE USED AS SEPARATION MEDIA IN THE METHOD

[75] Inventors: Jan Ericsson, Helsingborg; Eva Berggren, Uppsala; Liselotte Lundh, Rimbo, all of Sweden

[73] Assignee: Pharmacia Biotech AB, Uppsala, Sweden

[21] Appl. No.: 648,108

[22] PCT Filed: Nov. 17, 1994

[86] PCT No.: PCT/SE94/01090

§ 371 Date: Jul. 8, 1996

§ 102(e) Date: Jul. 8, 1996

[87] PCT Pub. No.: WO95/13861

PCT Pub. Date: May 26, 1995

[30] Foreign Application Priority Data

Nov. 17, 1993 [SE] Sweden .................................. 9303790

[51] Int. Cl.$^6$ ...................................................... B01D 15/04
[52] U.S. Cl. ...................... 210/638; 210/502.1; 210/635; 210/666; 502/401; 568/687
[58] Field of Search .......................... 210/198.2, 500.42, 210/634, 635, 638, 656, 666, 400, 502.1, 644, 649, 767; 502/401, 402, 404; 568/687, 688, 689, 691

[56] References Cited

U.S. PATENT DOCUMENTS

| | | | |
|---|---|---|---|
| 2,933,460 | 4/1960 | Richter et al. | 210/638 |
| 3,247,133 | 4/1966 | Chen et al. | 210/500.42 |
| 3,298,925 | 1/1967 | Mosbach | 210/635 |
| 3,450,630 | 6/1969 | Bloch et al. | 210/644 |
| 3,645,890 | 2/1972 | Lukach et al. | |
| 4,353,802 | 10/1982 | Hara et al. | |
| 5,114,577 | 5/1992 | Kusano et al. | 210/635 |
| 5,470,463 | 11/1995 | Girot et al. | 210/635 |

FOREIGN PATENT DOCUMENTS

| | | |
|---|---|---|
| 2047782 | 2/1992 | Canada . |
| 0525204 | 2/1992 | European Pat. Off. . |
| 4024517 | 11/1991 | Germany . |

*Primary Examiner*—Joseph W. Drodge
*Attorney, Agent, or Firm*—Birch, Stewart, Kolasch & Birch, LLP

[57] ABSTRACT

The present invention is directed towards a separation method comprising the steps: (i) contacting an aqueous liquid that contains a dissolved substance that is to be enriched with a polymer under conditions allowing selective partition of said substance to said polymer, whereafter (ii) said polymer containing said substance is removed from said aqueous liquid. The polymer employed is a poly(vinyl ether) having different or identical vinyl ether subunits (1) where X et Y are selected among hydrogen and methyl; and R is selected among organic groups. A plurality of R are equal to a hydrophilic organic group. One or more R comprise a bioaffinity ligand; an ion exchange group, etc. The method may be applied to bioseparations such as gel, affinity, ion exchange and covalent chromatography and corresponding batch procedures. Also disclosed are vinyl ether polymers that can be employed in the method.

18 Claims, No Drawings

METHOD FOR SEPARATION AND SYNTHETIC POLYMERS THAT CAN BE USED AS SEPARATION MEDIA IN THE METHOD

BACKGROUND OF THE INVENTION

The present invention concerns media for separations that involve partition of a desired substance or group of substances between a polymer and a liquid. The polymers used are normally called separation media and may be soluble or insoluble in the liquid. For the separation of biomolecules the liquid is often aqueous. According to the inventive concept, the polymer is a hydrophilic poly(vinyl ether).

Typically, insoluble separation media are based on hydrophilic porous matrixes built up of a synthetic polymer or a biopolymer, for instance poly(hydroxyalkyl methacrylate), dextran or agarose. The matrixes have been in form of beads, particles or monoliths (continuous forms). Often the surface of the matrix has been modified with a specific functionality in order to provide the actual interaction between solute molecules and ligands immobilised on the matrix.

Today, ion exchange is the most frequently used chromatographic technique for the separation of biomolecules. Other important techniques are gel filtration, hydrophobic interaction, reversed phase, metal chelate chromatography, covalent chromatography, and affinity chromatography. For a review se J-C. Janson et al (J-C. Janson et al., in "Protein Purification" VCH Publishers, Inc., 1989). The adsorption principles of these techniques have also been applied to other separation methodologies, for instance batch procedures, electrophoresis, centrifugation, etc.

Vinyl ethers have been suggested as monomers in radical polymerizations in order to synthesize chromatographic support particles (Hitatchi Chemical KK, Derwent Abstract 92-111582/14 (1992); Hitatchi Chemical KK, e.g. derwent Abstract 92-111583/14 (1992)). However, vinyl ethers are not susceptible to radical polymerization, which indicates that poly (vinyl ethers) are not enabled from this type of publications.

Poly(vinyl alcohols) are prepared by radical polymerization of vinyl acetate with subsequent ester hydrolysis. Due to hydrogen radical abstraction and head to head polymerization a significant amount of unstable/destabilized configurations such as vicinal diols and carbon-carbon branchings [—$CH_{3-n}$(—$C(-)_3)_n$, where n is 2 or 3] will be introduced.

The synthesis of essentially linear poly(vinyl ethers) containing a low number of vinyl ether subunits by living cationic polymerization has previously been described (S. Kanaoka et al., Macromolecules 24(21) (1991) 5741–5745; M. Minoda et al., Macromolecules 23(7) (1990) 1897–1901; M. Minoda et al., Macromolecules 25 (1992) 2796–2801; S. Kanaoka et al., J. Polym. Sci. 28 (1990) 1127–1136)) for alkyl vinyl ether, 2-acetoxyethyl vinyl ether, 2-hydroxyethyl vinyl ether, 2-aminoethyl vinyl ether, 3-dikarboxypropyl vinyl ether and esters and amides thereof, 2-carboxyethyl vinyl ether etc. See also S. Kanaoka et al., Macromolecules 24(21) (1991) 5741–5745; M. Minoda et al., Macromolecules 23(7) (1990) 1897–1901; M. Minoda et al., Macromolecules 25 (1992) 2796–2801; S. Kanaoka et al., J. Polym. Sci. 28 (1990) 1127–1136. The publications discuss the amphiphilic properties of the oligomers.

Living cationic polymerization of ethyl 2-(vinyloxy) ethoxyacetate with subsequent hydrolysis of pendant ester groups has enabled linear poly(vinyl ethers) containing a high number of vinyl ether subunits. The pendant group in the final polymer has uniformly been —$OCH_2CH_2OCH_2COOH$ (E. Takeuchi et al., J. Polym. Sci. 27 (1989) 3303–3314).

Requirements of Separation Media and Desired Improvements

The actual matrixes (separation media) to which a water-soluble substance is to be partitioned have to expose a high hydrophilicity towards an aqueous liquid, low unspecific interaction with proteins, pH-stability in the range of 2–14, etc. Improvements relative these variables are desirable. Moreover, it is of great interest to improve parameters related to surface chemistry including gel capacity and kinetics, which will give considerably higher productivity in a separation.

Strategy for the Invention

The above-mentioned improvements may be accomplished by utilizing separation matrixes providing surfaces with well-characterized hydrophilic polymers in contact with the aqueous liquid phase. Thus there is a demand for novel hydrophilic polymers, preferably linear, and their total synthesis including monomers. Suitable polymers should be able to functionalize with ion exchange groups, hydrophobic or hydrophilic moieties, affinity ligands etc; to cross-link; to bind to matrix carriers etc, for instance by physical adsorption (hydrophobic bonds) or covalent bonds (with preference for amino, ether and thioether bonds).

The appropriate monomers and polymerization conditions will enable control of the reaction to the effect that one reproducibly obtains well-characterized polymers that are optimal for the intended application (gel filtration media, affinity media, ion exchange media, polymer to be functionalized with various predetermined groups etc).

We have now realized that hydrophilic poly(vinyl ethers) will comply with the above-mentioned criteria. The preferred synthesis is cationic polymerizations (T. Higashimura et al., Compr. Polym. Sci., 3, 673 (1989)). For our purpose "living cationic polymerization" is likely to be extremely efficient because it may lead to polymers containing well-defined blocks and sequences of monomers within the polymer chain.

THE INVENTION

A first aspect of the invention is a novel separation method utilizing certain types of hydrophilic vinyl ether polymers. The method is defined under heading 2.5. A second aspect is novel hydrophilic vinyl ether polymers.

Definition of the Hydrophilic Poly(vinyl ethers) that can be used in the Inventive Separatin Method The characteristic feature of theses polymers is that they comprise a poly(vinyl ether) chain containing identical or different vinyl subunits. The subunits comply with Formula 1:

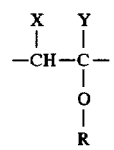

In order to be useful in water and other aqueous liquids the groups R are selected so that the polymer becomes hydrophilic. The polymer chain is essentially free from carbon-carbon branches and/or vicinal ether groups formed during the polymerization reaction [—CH$_{3-n}$(—C(—)$_3$)$_n$ where n is 2 or 3].

X and Y may be identical or different and are selected among hydrogen and methyl. In case one of them is methyl, it is preferred to be X.

R is selected among organic groups that provide an aromatic or saturated carbon atom attached directly to the oxygen atom. Appropriate organic groups are hydrophobic groups and hydrophilic groups. By saturated carbon is meant throughout the specification an sp$^3$-hybridized carbon atom only binding carbon and/or hydrogen and at most one oxygen or nitrogen or sulfur.

Examples of hydrophobic groups R are hydrocarbyl groups that are saturated or contain unsaturated structures, such as aromatic rings and other unsaturated carbon-carbon bonds etc. Specific examples are alkyl, arylalkyl, alkylaryl, alkenyl etc. Preferably the hydrocarbyl groups have 1–25, such as 1, 2, 3, 4 etc up to 20 or up to 15 carbon atoms. One or more hydrogen(s) of the hydrocarbyl group may be replaced with a functional group, preferably non-ionic, e.g. an alcoholic or a phenolic hydroxyl, an ester, an ether, a thioether etc. The molar ratio C/(O+N+S) usually is greater than 5.

Hyrophilic groups (R) contains a straight, branched or cyclic chain of sp$^3$-hybridized carbon atoms (saturated), to which chain hydrogens, saturated carbons and at least one hydroxy and/or amino group are bound. The chain may, at one or more positions, be broken by an oxygen or a nitrogen atom. There is at most one oxygen or nitrogen atom bound to one and the same carbon atom. The molar ratio (O+N)/C is greater than or equal to 0.5. The oxygen or nitrogen atom through which these groups are attached to the polymeric carbon skeleton is included in the sum (O+N). Illustrative examples are groups of 2–15 carbon atoms.

A particularly preferred group R is R'—B— where B is a hydrophilic organic bridge that may consist of a straight, branched or cyclic saturated carbon chain of 2–24, such as 2–12 sp$^3$-hybridized carbons. The chain may, at one or more positions, be broken by an oxygen or a nitrogen atom and/or contain at least one hydroxy and/or at least one primary amino (NH$_2$) group bound directly to one of said sp$^3$-hybridized carbon atoms. There is at most one oxygen or nitrogen atom bound to one and the same carbon atom in the chain. The molar ratio (O+N)/C in B is greater than or equal to 0.5. The sum (O+N) includes oxygen and nitrogen atoms binding directly to terminal positions of B. Preferably B complies with the formula [(CH$_2$)$_n$—O]$_m$ where n is an integer that may be 2–4 and m is an integer that may be 1–10.

R' (in R'—B—) is selected from OH, NH$_2$ and substituted forms thereof in which one respective one or two hydrogens has/have been replaced with an organic residue R". In case high hydrolytic stability is required for the substituted forms of OH and NH$_2$ groups, they preferably exist as an ether respective a secondary, tertiary or quartenary amine, i.e. the organic residue R" provides a saturated or aromatic carbon atom directly attached to the oxygen or nitrogen.

Thioether bonds are known to have about the same hydrolytic stability and basicity as ether bonds. Therefore, in the context of the present invention, thioether bonds are likely to function equivalently to ether bonds. This also implies that OH can be replaced by SH.

The organic residue R" may be selected from: groups comprising affinity ligands; groups enabling reversible disulfide binding of thiol compounds to the poly(vinyl ether) (e.g. covalent chromatography); pronounced hydrophilic groups; and groups rendering the poly(vinyl ether) insoluble in aqueous liquids (e.g. water).

Illustrative examples of affinity ligands are:

a. A member in a pair of compounds that exert biospecific affinity for each other (bioaffinity ligands). Examples of such pairs are antigens/haptens and antibody active entities (intact antibodies and their antibody active fragments (Fab, Fv, F(ab)$_2$ etc)); hormones and their receptors; IgG-binding proteins (Protein A, G and L) and IgG including fragments containing an Ig-constant region; complementary nucleic acids; complementary oligonucleotides; lectins and compounds containing carbohydrate structures; biotin and (strep)avidin etc.

b. Ion exchange groups selected among carboxy (—COO$^-$ bound to carbon), sulphonic acid (—SO$_3^-$ bound to carbon), phosphonic acid (—PO$_3^{2-}$ bound to carbon), primary, secondary, tertiary or quartenary amino (positively charged forms), zwitter ionic group containing both negatively and positively charged groups selected among the ones previously mentioned, and amphiphilic groups containing separate hydrophobic and ionic parts. The carbon atoms to which —COO$^-$, —SO$_3^-$ and —PO$_3^{2-}$ are attached are preferably saturated although they may also be aromatic. In addition to the ionic group these carbons only carry hydrogen and carbon.

c. Hydrophobic groups as defined for R above.

d. Chelate groups comprising a strongly chelated metal ion, e.g. the appropriate ions of zinc, iron, copper, cobalt etc.

e. Organic residues R" that enable reversible disulfide binding exhibit a functional group that is selected among: thiol (HS—), reactive disulfides (R$^1$—S—S—), thiolsulfonates (R$^2$—SO$_2$—S—) and thiolsulfenates (R$^3$—SO—S—), all of which with their free valence bound directly to a saturated carbon. R$^1$ is selected so that R$^1$—S—S— reacts quantitatively with thiol compounds in a thioldisulfide exchange reaction with release of a thiol (R$^1$—SH) that essentially quantitatively tautomerize to the corresponding thione (HR'$^1$=S). Typical examples of R$^1$ are 2-pyridyl and 4-pyridyl. R$^2$ and R$^3$ are in principle any organic group that provides a carbon (preferably saturated) next to the sulfur atom, which means that R$^2$—SO$_2$—S— and R$^3$—SO—S— analogously to R$^1$—S—S— will form disulfides with thiol compounds. The expression "reversible disulfide binding" means that the disulfide is able to be split by the presence of an excess of a low molecular weight thiol compound.

f. Hyrophilic groups as defined for R above. Additional examples are polymeric residues of water-soluble polymers, for instance polysaccharides, such as dextran, hydroxyethyl starch, carboxy methyl cellulose etc. Polymeric residues R" may also comprise one or more repeating subunits of formula I linked to the oxygen or nitrogen atom of HO—B— or NH$_2$—B—, respectively.

The poly(vinyl ether) may be insoluble in aqueous liquid media. Insolubility may be caused by the presence of subunits of formula 1 wherein R' is a substituted form of OH or NH$_2$ in which at least one hydrogen is replaced with an organic residue (R") selected among:

g. groups that are covalent attached to a support (matrix carrier) that is insoluble in the aqueous liquid media; and h. groups providing insolubility by inter- and/or intramolecular crosslinking of the poly(vinyl ether) chain.

Insolubility may also be caused by the presence of subunits of formula 1 in which i. hydrophobic groups R or hydrophobic organic residues R" in R' are physically adsorbed to a hydrophobic support (matrix carrier) that is insoluble in the aqueous liquid media.

Preferably insolubility is caused by covalent attachment via a substituted form of said OH or $NH_2$ group (g above).

Insolubility may also be caused by attachment to matrix carriers at positions other than those explicitly mentioned above, for instance at a terminal position of the linear polymer chain (see below).

Water-insoluble matrix carriers may be of different physical forms such as beads, monoliths, balls, particles, tube walls, membranes etc. The matrix carriers may by organic or inorganic. They may be porous or non-porous. The material of the matrix carriers may be hydrophilic and based on insoluble polysaccharides like agarose or crosslinked dextran. The matrix carrier may also be hydrophobic, e.g. by being made from polystyren.

The poly(vinyl ether) used in the present invention is represented by Formula 2:

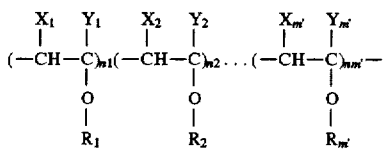

where the free terminal valences binds to groups that have been introduced via the initiation and termination, respectively, of the polymerization, including derivatized such groups. The free valence to the left may bind to a hydrogen or a carbon of an initiating carbocation. The free valence to the right may bind to a vinyl group (loss of hydrogen ($H^+$) from the lastly added monomer) or to a group formed by reaction of the carbocationic center of the propagating chain with a Lewis base, such as a carbanion [$^-C(-)_3$, where $(-)_3$ represents bonds to groups that enables the formation of the carbanion] and an alcohol and the corresponding alkoxide ion. Alkoxide ions give acetal end groups ($Y_{m'+1}$=hydrogen) or ketal end groups ($Y_{m'+1}$=methyl), and carbanion gives ether functions [—C($OR_{m'+1}$)$Y_{m'+1}$—C(-)$_3$]. "m'+1" indicates that it is a rightly positioned terminal subunit. A typical example of a useful carbanion is malonic acid diester anion [$^{-CH(COOR}{}_a)_2$ with $R_a$=alkyl or aryl)] that gives —$CY_{m'+1}(OR_{m'+1})CH(COOR_a)_2$ as the end group. Lewis bases such as ammonia and primary amines result in instable end groups. Terminal groups introduced due to the initiation and/or termination reactions may in many cases be further processed and employed for specific purposes. For instance —$CY_{m'+1}(OR_{m'+1})CH(COOR_a)_2$ may be hydrolysed to —$CY_{m'+1}(OR_{m'+1})CH(COOH)_2$ which in turn may be decarboxylated to —$CY_{m'+1}(OR_{m'+1})CH_2COOH$ and subsequently covalently attached to a matrix carrier carrying hydroxyl or amino groups.

$R_1, R_2 \ldots R_{m'}$ are groups selected in the same manner as R (in formula 1 above). They are selected, for instance, among (i) hydrophobic groups, such as hydrocarbyl groups, and hydrophilic groups, and (ii) $R_1$=$R'_1$—$B_1$—, $R_2$=$R'_2$—$B_2$— ... $R_m$=$R'_{m'}$—$B_{m'}$—. $R'_1, R'_2 \ldots R'_{m'}$ and $B_1, B_2 \ldots B_{m'}$ are selected in the same way as R' and B, respectively.

$X_1, X_2, X_3 \ldots X_m$ and $Y_1, Y_2, Y_3 \ldots Y_m$ are selected in the same manner as X and Y above.

$n_{m'}$ is an integer giving the number of blocks containing identical repeating vinyl subunits. For any given block at least one of X, Y and R differs from its counterpart in the closest neighbouring block(s).

$n_1, n_2, \ldots n_{m'}$ are integers greater than zero and $n_1+n_2+\ldots+n_{m'}=n$, where n is the number of vinyl ether subunits in the linear polymer chain. n is preferably <20 000, such as <15 000. For the polymer as such novelty exist for longer chains, i.e. n>150, such as >200 or >300 or >500 or >1000. For the separation method defined under subheading 2.5, the lower limit may potentially be equal to 10, 50, 100, 200, 300, 500 or 1000.

B may be uniform for essentially all vinyl subunits in which R complies with R'—B—.

In order to provide the sufficient hydrophilicity, a plurality, preferably at least 5%, such as at least 25%, of the vinyl subunits of the linear polymer chain have R groups selected among the above-mentioned hydrophilic groups. Suitable Rs ($R_1, R_2 \ldots R_m$) are selected among HO—B—, $H_2N$—B— and substituted forms thereof in which a hydroxy hydrogen or an amino hydrogen is replaced with the above-mentioned hydrophilic group (organic residue, R"). The corresponding upper limit is often 75% and in some cases essentially 100%.

Organic residues R" in accordance with alternatives a, b, c, d, e, g, h or i is present in at least one R. Illustrative upper limits for each of these alternatives are 50% or 75%.

Polymers defined in formula 2 (with vinyl subunits as defined in formula 1 and n>150) in which OH and/or $NH_2$ are present together with substituted forms thereof according to at least one of a, b, c, d, e, f, g, h and i are novel as such.

A particular embodiment of the invention is the complex formed during a separation (as defined under subheading 2.5) between the vinyl polymer and the substance to be partitioned to the polymer. Examples of substances that may complex with polymers of the present invention are bioorganic molecules, such as proteins and polypeptides, lipids, carbohydrates, nucleic acids, oligonucleotides, nucleotides, steroids, amino acids etc. The substance is complexed to the vinyl polymer due to (a) disulfide linked groups introduced by the use of thiol exchange reactions as defined above for reversible disulfide binding or (b) organic residues R" exhibiting groups selected from affinity groups (e.g. bioaffinity groups, ion exchange groups, metal chelate groups, hydrophobic groups as defined above).

Monomer Synthesis

Vinyl ethers as such are well adapted to cationic polymerization. However, the present invention requires introduction of nucleophilic/hydrophilic groups, the presence of which is forbidden during cationic polymerization. As a consequence protecting groups have to be introduced into the monomers to be used.

It has been shown by Sawamoto et al. (Sawamoto et al., Macromolecules, 18, 2097 (1985)) that 2-acetoxyethyl vinyl ether (AcOVE) may be synthesized by the route (Formula 3):

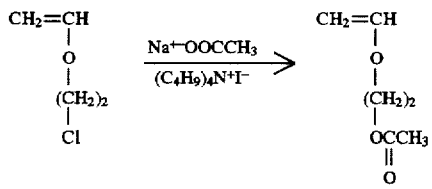

AcOVE may also be obtained by acetylation of 2-hydroxyethyl vinyl ether (HEVE).

A convenient protecting group may be introduced by the reaction of HEVE with di-tert-butyl dicarbonate (Formula 4):

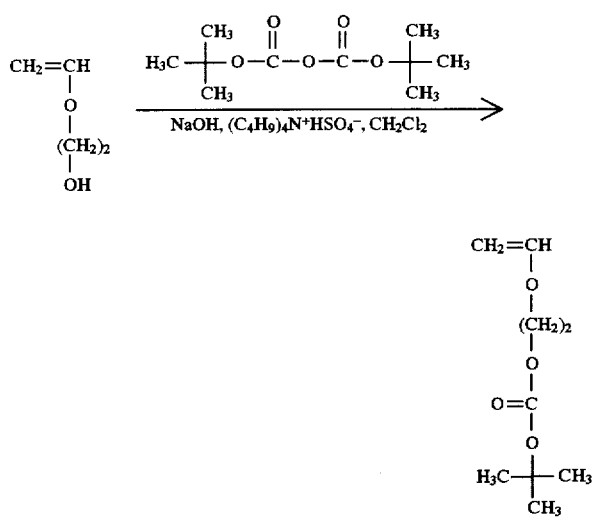

Formulae 3 and 4 give two protecting groups which have different inherent stability towards acid and base. The acetoxy group may be removed under alkaline conditions while the t-BOC group may be removed by acid (M. Bodansky et al., "The Practice of Peptide Synthesis", Springer-Verlag, Berlin, 1984). The t-BOC protecting group is advantageous in our case because it will undergoes acid-catalyzed elimination to give gaseous side products and the desired vinyl hydroxyalkyl ether polymer in solution (J. M. J. Fréchet et al., Polym. J., 19, 31 (1987); J. Ericsson et al., Makromol. Chem., 192, 1621 (1991)). The reaction will be (Formula 5):

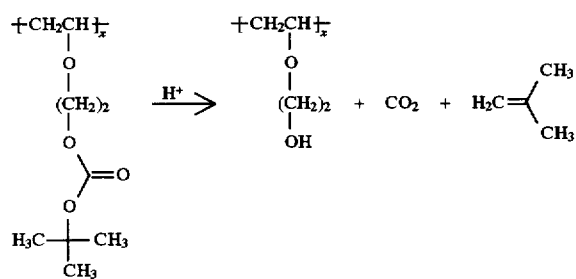

A third protecting group that can be used is the t-butyl dimethyl siloxyl group.

Phthalimide as protecting group has been described by Higashimura et al. (T. Hashimoto et al., J. Polym. Sci.: Part A: Polym. Chem., 26, 3361 (1988)) (Formula 6):

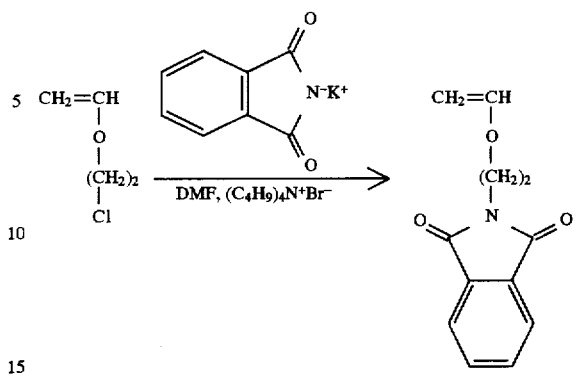

After polymerization the deprotection is accomplished by hydrazine and poly(2-aminoethyl vinyl ether) is obtained Further protecting groups for amino and hydroxy groups are given in text-books. See Protective Groups in Organic Chemistry (T W Greene, John Wiley & Sons, 1981).

Polymer Synthesis

General Features of Cationic Polymerization

Polymerizations are considered "cationic" when they involve a positively charged active species acting as an electrophile towards the monomer. Vinyl ethers (Formula 7)

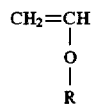

which have a strongly electron-donating alkoxy substituent, readily form polymers on treatment with an acid, i.e. the chain growth is activated by an acidic initiator, such as a protonic acid, Lewis acid or more recently by different "Living Systems" (J. P. Kennedy/Béla Iván, Design Polymers by Carbocationic Macromoleculear Engineering: Theory and Practice, Carl Hanser Verlag, Munich, Germany)).

Wislicenus reported 1878 the transformation of ethyl vinyl ether into a viscous material when iodine was present (J. Wislicenus, Justus Liebigs Ann. Chem., 92, 106 (1878)). The first systematic investigations of vinyl ether polymerization began in 1928 at I. G. Farbenindustrie in Germany. For a review see Schildknecht et al (C. E. Schildknecht, "Vinyl and Related Polymers", Wiley, New York, 593 (1952)). Two decades later, in 1947, Schildknecht et al (C. E. Schildknecht et al., Ind Eng. Chem., 39, 180 (1947)) recognized that poly(isobutyl vinyl ether) obtained with the Lewis acid boron trifluoride or its etherate ($BF_3OEt_2$), is either crystalline (nontacky) or amorphous (tacky) depending on the polymerization conditions.

Up to know various Lewis acids have been used for the initiation of cationic polymerizations. A representative formula is $MtX_n$ (Mt=metal including boron; X=halogen; and n is a figure that makes $MtX_n$ a Lewis acid).

Synthesis of Poly(vinyl ethers)

At the priority date our choice of Lewis acid is $BF_3O(Et)_2$, which gives an initiating proton when reacting with traces of water present in the polymerization system.

A general polymerization route for a vinyl ether is (Formula 8):

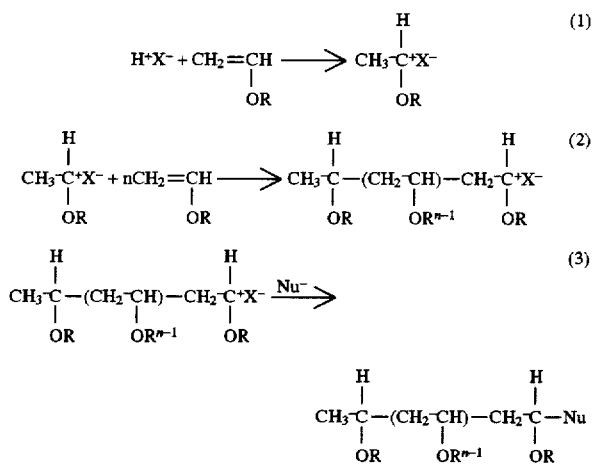

The steps in the reaction are: (1)=initiation; (2)=propagation; (3)=termination.

By using protected forms of 2-aminoethyl vinyl ether and 2-hydroxyethyl vinyl ether, polymerizing and finally deprotection, we have been able to synthesize poly(2-hydroxyethyl vinyl ether), poly(2-aminoethyl vinyl ether) and the analogous copolymers containing both amino and hydroxy groups in predetermined ratios. By adding vinyl hydrocarbyl ethers to the polymerization mixture, blocks of subunits where R is a purely hydrophobic group may be introduced into the chain.

Derivatization of Poly(vinyl ethers)

Deprotection leads to introduction of OH— and/or NH$_2$-groups allowing attachment of various organic residues R".

Methods for attaching an organic residue R" to OH and/or NH$_2$ groups in a polymer are well known in the prior art. They often make use of bifunctional compounds A-(bridge)$_n$-C where (a) n may be 1 or 0,
(b) A is a reactive function that is capable of forming a covalent link to an amino group or hydroxy group (for instance HO—B— or H$_2$N—B—) of the base polymer (of formula 2),
(c) the term "bridge" represents an organic bridge, and
(d) C is a group possessing the property/function that is to be linked to the vinyl polymer or a group that may be transformed to said function/property.

The methods comprise contacting a poly(vinyl ether) of formula 2 exhibiting HO— and/or —NH$_2$ groups with a bifunctional compound A-(bridge)$_n$-C under conditions permitting formation of a covalent link between A and an HO— or H$_2$N-group of the poly(vinyl ether), followed, if necessary, by transformation of C to the desired group and deprotection and derivatization of further HO— and/or NH$_2$-groups to introduce other organic residues R".

Preferably A is selected so that an ether or amino (secondary, tertiary or quartenary) linkage is created. Illustrative examples of A are epoxides and the analogous nitrogen group (in which —O— is replaced with —NH—), halohydrins, vicinal alkyl dihalides, alkyl halides in which the halo atom is α to an sp$^2$-carbon, and certain C—C double bonds that are directly attached to a strongly electron-withdrawing substituent.

The organic bridge is inert, preferably containing only hydrocarbyl groups, ether groups and other groups hard to hydrolyse. By the term "inert" is contemplated that, under the conditions employed, the bridge does not detonate or participate in side reactions. For n=0 the meaning of "bridge" becomes redundant.

The group C is selected among the same reactive groups as A. C may in addition be a matrix carrier (including soluble and insoluble polymers) which have been activated to contain the reactive group A.

Certain bifunctional reagents are structurally monofunctional but with a reactive function that enables them to react twice with nucleophiles. Examples are CNBr, carbodiimides, and carbonyl diimidazole. For this special type of reagents n equals 0 and A becomes structurally non-distinctive from C.

Cationic and Anionic Exchanger Synthesis

Ion exchanging polymers of formula 2 can be obtained by reacting a bifunctional compound A-(bridge)$_n$-C as defined above in which C is an anion or cation exchanging group or a group transformable to such a group, with a polymer of formula 2 containing HO— and/or NH$_2$-groups. The reaction conditions applied, selection of starting poly(vinyl ether), possible subsequent steps to introduce other organic residues R" bound to said HO— and/or NH$_2$-groups, and preferred options among these variables are as outlined under subheading 2.4 above. One suitable mode is to start with a water-soluble poly(vinyl ether), introduce the ion exchange organic residue, and in a subsequent reaction attach the derivatized ion exchange vinyl ether polymer to a matrix carrier (support).

Illustrative examples of bifunctional compounds are allyl halides (that after reaction with the polymer may be further processed with bisulfite or primary or secondary amines to introduce sulphonic acid groups or amino groups, respectively). N,N-diethyl aminoethyl chloride hydrochloride, glycidyl trimethylammonium chloride, α-halo acetic acids etc.

The number of ion exchanging groups introduced is controlled by the relative amount of free (deprotected) OH— and NH$_2$-groups in the starting polymer, the relative amount of added bifunctional compound (A-(bridge)$_n$-C) and the reactivity and selectivity of the reactive group A etc.

Attachment of Other Groups Permitting Specific Interactions (Hydrophobic Groups, Metal Chelate Groups, Reactive Disulfide Group and Bioaffinity Ligands)

The general principle for introduction of organic residues R" outlined in subheading 2.4 above is applicable, except for the bifunctional compound A-(bridge)$_n$-C now being selected so that C contains a group according to a–e above or a group that is transformable to a group containing one of these groups. The reaction conditions applied, selection of starting poly(vinyl ether), and possible subsequent steps to introduce other organic residues are in analogy with what has been said under subheading 2.4 above.

Attachment of the Polymer to a Matrix Carrier (Support)

The attachment reaction is carried out by the standard procedures outlined above under heading 2.4. The starting poly(vinyl ether) exhibits HO— and/or H$_2$N-groups as defined for formula 1 and may be either water-soluble or water-insoluble. The polymer may in addition exhibit vinyl subunits carrying organic residues R" according to at least one of a–f of formula 1, with preference for residues carrying ion exchange or hydrophobic groups. In the bifunctional compound A-(bridge)$_n$-C the group A and "bridge" have the same meaning as indicated under heading 2.4. The group C is restricted to comprise a matrix carrier or a group that can form a hydrophobic adsorptive link or a covalent link to a matrix carrier.

The attachment reaction comprises reacting the bifunctional compound A-(bridge)$_n$-C with a polymer as defined in formula 2 under conditions allowing formation of a covalent bond between A and the polymer, whereafter, if C does not comprise a matrix carrier, binding of C to a matrix carrier. The vinyl ether polymer may be further derivatized for instance by introduction of one or more organic residues R".

In the alternative the polymer may also be adsorbed physically to the matrix carrier, for instance the poly(vinyl ether) exhibits hydrocarbyl groups and the matrix carrier is hydrophobic.

The matrix carrier (support) may be soluble or insoluble in aqueous media like water.

The inventive polymer may also form its own insoluble matrix carrier by being crosslinked by the aid of a bifunctional compound A-(bridge)$_n$-C in which both A and C are capable of forming covalent bonds with OH— or NH$_2$-groups.

General Applications of the Inventive Polymers

The poly(vinyl ether) described herein may be used according to separation principles comprising the steps:

a. contacting an aqueous liquid that in dissolved form contains a substance (including a group of substances) that is to be enriched with a polymer under conditions allowing selective partition to said polymer of said substance or group of substances, whereafter b. said polymer or part thereof containing the substance or group of substances is removed from said aqueous liquid.

Previously used polymers in this type of separations have been soluble or insoluble in the aqueous liquids used.

The substance(s) partitioned to the polymer may be contaminants that are to be removed or substance(s) that one desires to isolate. In the former case, working up is continued with the remaining aqueous liquid. In the latter case working up is continued with the polymer.

The aqueous liquid is often water.

The general method comprises different chromatographic procedures, batch procedures, electrophoresis in gels and other suitable matrixes, adsorptions performed in immunoassays, centrifugations utilizing partition into polymers, membrane filtrations, separation methods based on complexation, precipitation and sedimentation by the aid of a polymer.

According to the inventive concept, the characteristic feature is that the polymer complies with formula 2, i.e. a polymer having vinyl ether subunits as defined in formula 1, and that this polymer is in direct contact with the aqueous liquid media during the partition step (step a above).

Subaspects of this aspect of the invention utilize

A. the polymer of formula 2 as a matrix for gel filtration (the subunits exhibit free OH groups including organic residues according to f and optionally also groups/residues according to g, h and i as defined for formula 1), or B. adsorption/partition techniques based on that the vinyl polymer of formula 2 carries at least one type of organic residues R" which provides for binding/interaction between the substance to be separated and the polymer (the subunits exhibit e.g. groups a, b, c, d and e as defined for formula 1).

For illustrative purposes separation by chromatography will be discussed in detail.

Separation by chromatography depends on the differential partition of biomolecules between a stationary phase (the chromatographic media) and a mobile phase (the buffer solution, aqueous liquid phase). Normally the stationary phase is packed into a vertical column of plastic, glass or stainless steel, whereas the buffer is passed through this column.

Since the development of the first cellulose ion exchangers by Peterson and Sober (E. A. Peterson et al. J. Am. Chem. Soc., 78, 751 (1956)) and of the first practical gel filtration media by Porath and Flodin (J. Porath et al., Nature, 183, 1657 (1959); J-C Janson, Chromatographia, 23, 361 (1987)) a variety of adsorbents has been introduced which exploit various properties of proteins. Important properties and corresponding chromatographic methods are:

a. Size and shape—Gel Filtration
b. Net charge—Ion Exchange Chromatography
c. Isoelectric point—chromatofocusing
d. Hydrophobicity—Hydrophic Interaction Chromatography Reversed Phase Chromatography
e. Metal binding—Metal Ion Affinity Chromatography
f. Content of exposed thiol groups—Covalent Chromatography
g. Biospecific affinities for ligands, inhibitors, receptors, antibodies etc.—Affinity Chromatography The underlying binding/partition principle is applicable also to other separation techniques such as batch procedures, electrophoresis, centrifugations etc.

The inventive method is particularly adapted for the separation of compounds exhibiting protein or polypeptide structure, lipid structure, carbohydrate structure, nucleic acid or oligonucleotide or nucleotide structure, steroid structure, amino acid structure etc.

The evaluation of the new polymers described in this work has so far been performed by Gel Filtration and Ion Exchange Chromatography.

Gel Filtration Chromatography

In gel filtration, molecules in solution are separated according to differences in their sizes as they pass through a column packed with a gel chromatographic media. Suitable media have a carefully controlled pore range size and are often formed by crosslinking a suitable hydrophilic polymer to a three-dimensional net-work.

Composite gels may be prepared by grafting a second polymer onto a pre-formed matrix. In Superdex® dextran chains are covalently bonded to a highly cross-linked agarose gel matrix (Superdex® and Superose® (below) are trademarks of Pharmacia BioTech AB, Sweden)

We have grafted poly(2-hydroxyethyl vinyl ether) onto Sepharose® HP (based on cross-linked agarose) and evaluated the product obtained by comparison with Superdex® 30 PG. This type of composite matrix will lead to a more well-defined system, because the synthetically made vinyl ether-based polymers may be varied in composition practically as desired. Polymer parameters to be varied are the molecular weight and its distribution, hydrodynamic volume which depend on the side groups of the polymer etc.

The comparison has involved parameters such as tendency for undesirable interactions and selectivity curves. It has been clearly shown that poly(2-hydroxyethyl vinyl ether) attached to Sepharose® HP possesses the same or better characteristics as Superdex® 30 PG in a representative gel filtration application.

Adsorption Chromatography

Adsorption chromatography depends upon interactions of different types between solute molecules and ligands immobilized on a chromatographic matrix. Affinity chromatography, ion exchange chromatography, covalent chromatography, metal chelate chromatography and hydrophobic interaction chromatography are illustrative examples of adsorption chromatography.

In this work the synthetically made cation exchange polymer of formula 10 grafted onto Sepharose® HP, and the anion exchange polymer of formula 9 grafted onto Sepharose® HP were compared with representative commercial products from Pharmacia AB.

Best Mode

The best experimental results so far has been accomplished with the chromatographic supports presented in the experimental part. However the inventors believe that better results will be obtained with poly(vinyl ethers) produced by the so called "living" or "controlled" cationic polymerization.

Experimental

Materials

2-Chloroethyl vinyl ether (98%), allyl bromide (98%) and boron trifluoride ethyl etherate (48% $BF_3(O(C_2H_5)_2)$) were purchased from Fluka (Schweiz). 2-hydroxyethyl vinyl ether (98.5%) was from Nisso Marutzen (Japan). Sodium acetate, tetra-n-butylammonium hydrogen sulphate (98%), magnesium sulphate (anhydrous) and Celite 545 were all from Merck Germany). Di-tert-butyl dicarbonate (97%), tetra-n-butylammonium iodide (98%), tetra-n-butylammonium bromide (99%), potassium phthalimide (99%) and hydrazine monohydrate (99%) were purchased from Janssen (Belgium). Sodium hydride (80% dispersion in mineral oil), sodium bisulfite and calcium hydride (95+%) were from Aldrich (Germany). Transferrin, ovalbumin, β-lactoglobulin, ribonuclease, aprotinin and Vitamin B12 were all from Sigma (U.S.A.). Glycidyltrimethylammonium chloride was supplied by Pharmacia AB (Sweden). The chemicals were used without further purification.

Toluene, hexane and methylene chloride used for the polymerizations, were from Aldrich (U.S.A.) and supplied in sure seal bottles. Dimethylformamide (99.5%) was from Jansen (Belgium). The other solvents were purchased from Labkemi (Sweden). The solvents were used without further purification.

Analysis

The synthesized monomers and polymers were characterized by FTIR using a Perkin Elmer 16PC FTIR and by $^1H$ and $^{13}C$ NMR using a JEOL EX270. The elemental analysis was conducted by Mikro-Kemi AB in Uppsala, Sweden. The MWD of the polymers were determined by gel permeation chromatography (GPC) in THF on a Waters GPC-system equipped with two polystyrene gel columns (Ultrastyragel® $10^4$Å and Ultrastyragel® $10^3$Å; 7.8×300 mm each (U.S.A.) ). The number-average molecular weight ($M_n$) and the polydispersity ratio ($M_w/M_n$) were calculated from GPC curves on the basis of a polystyrene calibration. Ultrafiltration was carried out on a Filtron Ultrapump II equipped with Ultrasette filters 8K and 30K respectively. The gel filtration was carried out on a Liquid Chromatography system. The glass column had an inner diameter of 10 mm and the bead height was 30 cm. The eluent flow was 0.5 cm/min. The buffer solution was 50 mM sodium phosphate +100 mM sodium chloride which gives a pH=7.4. The detector was a single path monitor UV 1® at 280 nm (Pharmacia AB, Sweden).

Monomer Synthesis

EXAMPLE 1

2-Acetoxyethyl vinyl ether

A 1000 ml three-necked flask was charged with sodium acetate (164 g, 2 mol), 2-chloroethyl vinyl ether (250 ml, 2 mol), 2-chloroethyl vinyl ether/2-acetoxyethyl vinyl ether (1/1) (200 ml) and tetra-n-butylammonium iodide (2 g). The reaction mixture was refluxed overnight (approximately 12 hours), with magnetic stirring and under argon atmosphere. After cooling to room temperature 250 ml distilled water and 300 ml diethyl ether were added. The organic phase was further washed with 3×100 ml distilled water, 3×150 ml 1M HCl, 5×100 ml distilled water and 4×100 ml brine. Drying with magnesium sulphate, filtration through Celite 545, evaporation of the solvent and finally distillation gave 200 g of the crude product as a slightly yellow liquid. An additional distillation over calcium hydride gave 160 g (yield 62% based on sodium acetate) of pure 2-hydroxyethyl vinyl ether as a colourless liquid. Boiling point 75° C/35 mbar. The product was confirmed by $^1H$ NMR (CDCl$_3$) δ (ppm) =2.1 (s,3H), 3.90(m,2H), 4.05(d,1H), 4.20(d,1H), 4.30(m, 2H), 6.47(m,1H).

EXAMPLE 2

2-(Tert-butoxycarbonyloxy)ethyl vinyl ether

Di-tert-butyl dicarbonate (51.3 g, 235 mmol), 2-hydroxyethyl vinyl ether (20 g, 227 mmol) and tetrabutylammonium hydrogen sulphate (2.8 g, 8 mmol) was dissolved in 200 ml methylene chloride. At 0° C., a prechilled sodium hydroxide (30%, w/w) solution was added dropwise with vigorous magnetic stirring for 5 hours. The organic phase was washed with 3×100 ml brine, dried with magnesium sulphate and evaporation of the solvent gave the crude product as a colourless liquid.

Distillation gave 26 g (yield 61% based on di-tert-butyl dicarbonate) of the pure 2-(tert-butoxycarbonyloxy)ethyl vinyl ether as a colourless liquid. Boiling point 69° C./2mbar. The product was confirmed by $^1H$ NMR (CDCl$_3$) δ (ppm)=1.5 (s,9H), 3.90(m,2H), 4.05(d,1H), 4.20(d,1H), 4.30(m,2H), 6.47(m,1H).

EXAMPLE 3

2-vinyloxyethyl phthalimide

A 1000 ml three-necked flask was charged with potassium phthalimide (100 g, 540 mmol), 2-chloroethyl vinyl ether (100 g, 940 mmol), tetra-n-butylammonium bromide (2 g) and 250 ml dimethylformamide. The reaction mixture was refluxed at 100° C. overnight (approximately 12 hours), with magnetic stirring and under argon atmosphere. After cooling to room temperature, the reaction mixture was poured into 1000 ml of distilled water which precipitates the crude product. Filtration and recrystallization from 3×500 ml methanol and 2×500 ml ethyl acetate with charcoal treatment and drying in the last step with magnesium sulphate gave 55 g (47% based on potassium phthalimide) of the pure 2-vinyloxyethyl phthalimide as slightly yellowish needles. The product was confirmed by $^1$H NMR (CDCl$_3$) δ (ppm) =3.95 (s,2H+2H+1H), 4.20(d,1H), 6.40(m,1H), 7.70(m,2H), 7.85(m,2H).

Polymer Synthesis

General

All of the equipment used in these polymerizations were dried at 110° C. overnight, and kept under argon atmosphere during the experimental procedures.

Synthesis Procedures

EXAMPLE 4

Poly(2-acetoxyethyl vinyl ether)

In a representative example a solution of 2-acetoxyethyl vinyl ether(15 ml, 118 mmol) and 50 ml toluene was cooled to −45° C. To the cooled monomer solution, 600 ml (gives 6·10$^{-2}$ mmol BF$_3$(O(C$_2$H$_5$)$_2$) of a pre-cooled initiator/toluene solution was added. After this the temperature was allowed to increase up to −20° C. which was the polymerization temperature. Finally the reaction was terminated after one hour with methanol. The polymer was characterized by FTIR: (1736, 1380, 1234, 1116 and 1054 cm$^{-1}$). GPC (M$_w$=200 000; M$_n$=80 000; H=2.5) and DSC (Tg=−25° C.).

EXAMPLE 5

Poly(2-(tert-butoxycarbonyloxyethyl) vinyl ether)

In a representative example 2-(tert-butoxycarbonyloxyethy) vinyl ether (0.5 ml, 2.7 mmol) was cooled to 0° C. and 10 μl (gives 1·10$^{-3}$ mmol BF$_3$O(C$_2$H$_5$)$_2$ of a pre-cooled initiator/toluene solution was added. The bulk polymerization was terminated after one hour with cold methanol. The polymer was characterized by FTIR: (1750, 1370, 1220, and 1076 cm$^{-1}$). GPC (M$_w$=429 000; M$_n$=110 000; H=3.9).

EXAMPLE 6

Poly(2-vinyloxyethyl phthalimide)

Typically, 2-vinyloxyethyl phthalimide (50 g, 230 mmol) was dissolved in dichloromethane and the solution was cooled to −30° C. To the cooled monomer solution, 2.5 ml (gives 2.5·10$^{-1}$ mmol BF$_3$(O(C$_2$H$_5$)$_2$) of a pre-cooled initiator/dichloromethane solution was added. After this the temperature was allowed to increase up to −20° C. which was the polymerization temperature. Finally the reaction was terminated after one hour with a cold methanol. The solvent was evaporated and the polymer was characterized by FTIR: (1772, 1708, 1390, and 1320 cm$^{-1}$), GPC (M$_w$=27 000; M$_n$=17 000; H=1.6) and DSC (Tg=64° C.).

EXAMPLE 7

Poly(2-vinyloxyethyl phthalimide-co-2-acetoxyethyl vinyl ether)

Typically, 2-vinyloxyethyl phthalimide (10 g, 46 mmol) and 2-acetoxyethyl vinyl ether (6 ml, 47 mmol) was dissolved in 60 ml dichloromethane and the solution was cooled to −30° C. To the cooled monomer solution, 600 ml (gives 6·10$^{-2}$ mmol BF$_3$(O(C$_2$H$_5$)$_2$) of a pre-cooled initiator/dichloromethane solution was added. After this the temperature was allowed to increase up to −20° C. which was the polymerization temperature. Finally the reaction was terminated after one hour with a cooled solution of 7N ammonia in methanol. The solvent was evaporated and the polymer was characterized by elemental analysis (C$_{theoretical}$=62, C$_{obtained}$=61.8; O$_t$=28, O$_o$=29.0; N$_t$=4; N$_o$=3.6; H$_t$=6; H$_o$=6.4; GPC (M$_w$=67 000; M$_n$=27 900; H=2.4) and DSC (Tg=22° C.).

Polymer Deprotection

EXAMPLE 8

Poly(2-hydroxyethyl vinyl ether)

The poly(2-acetoxyethyl vinyl ether) from example 4 was dissolved in 200 ml tetrahydrofuran. To this solution, 138 ml 1M NaOH(aq) was added in portions over a six hour period and the solution was allowed to stand for 48 hours at room temperature, with magnetic stirring. After this the reaction mixture was neutralized with 2M HCl(aq). The solvent was evaporated and further ultrafiltration removed the salt residues and also polymers/oligomers of molecular weights approximately below 30 000. Finally the pure product was freeze dried. The polymer was identified by FTIR (the carbonyl peak at 1736 cm$^{-1}$ disappeared).

EXAMPLE 9

Poly(2-aminoethyl vinyl ether)

The poly(2-vinyloxyethyl phthalimide) from example 6 was dissolved in 600 ml dichloromethane and 250 ml methanol. To this solution, 24 ml hydrazine monohydrate was added. The reaction mixture was allowed to stand for 14 hours at room temperature with magnetic stirring. After this all of the solvent was evaporated and 500 ml of distilled water and 250 ml 2M HCl(aq), was added. This solution was refluxed for 45 minutes. After cooling the solid residue was filtrated and the remaining solution was neutralized with 2M NaOH(aq). The solution was now concentrated and further ultrafiltration removed the salt residue and also polymers/oligomers of molecular weights approximately below 8 000. Finally the pure product was freeze dried. The polymer was identified by FTIR (the peaks at 1772 and 1708 cm$^{-1}$ disappeared.

EXAMPLE 10

Poly(2-aminoethyl vinyl ether-co-2-hydroxyethyl vinyl ether)

The poly(2-vinyloxyethyl phthalimide-co-2-acetoxyethyl vinyl ether) from example 7 was dissolved in 200 ml tetrahydrofuran. To this solution, 138 ml 1M NaOH(aq) was added in portions over a six hour period and the solution was allowed to stand for 48 hours at room temperature, with magnetic stirring. After this the reaction mixture was neutralized with 2M HCl(aq). The solvent was evaporated and further ultrafiltration removed the salt residues and also polymers/oligomers of molecular weights approximately below 8 000.

This partly deprotected polymer was dissolved in 50 ml distilled water and 4.4 ml hydrazine monohydrate. The reaction mixture was allowed to stand for 14 hours at room temperature with magnetic stirring. After this the pH was lowered to approximately 1–2 by the addition of 2M HCl (aq). This solution was refluxed for 45 minutes. After cooling the solid residues were filtrated off and the remaining solution was neutralized with 2M NaOH(aq). The solution was now concentrated and further ultrafiltration removed the salt residues and also polymers/oligomers of molecular weights approximately below 8 000. Finally the pure product was freeze dried. The polymer was identified by FTIR (the peaks at 1772, 1736 and 1708 $cm^{-1}$, respectively, disappeared.

Polymer Functionalization

EXAMPLE 11

Poly(2-aminoethyl vinyl ether-co-2-hydroxyethyl vinyl ether) functionalized with glycidyltrimethylammonium chloride Formula 9. Reaction formula for the synthesis of a anion exchanging polymer.

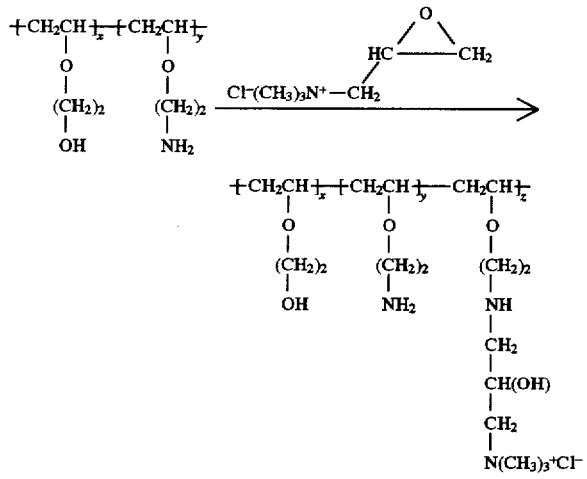

The copolymer from example 10 was dissolved in water together with glycidyltrimethylammonium chloride (GMAC) at pH=10 at room temperature. The GMAC concentration was kept at 75% level of the primary amino groups of the polymer. The reaction mixture was allowed to stand for 5 hours and the product in solution was used directly for the subsequent coupling reaction.

EXAMPLES 12–13

Synthesis of a Cation Exchanger

Reaction formula (Formula 10) for the synthesis of a cation exchanging polymer.

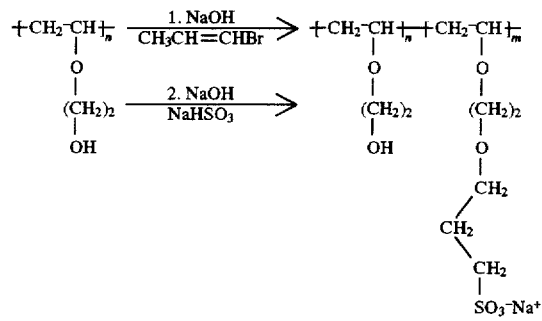

EXAMPLE 12

Poly(2-hydroxyethyl vinyl ether-co-2-allyloxyethyl vinyl ether)

In a representative example the poly(2-hydroxyethyl vinyl ether) (2 g, 22 mmol OH-groups) from example 8 was dissolved in 50 ml NaOH(aq) (30% w/w) and allylbromide (2.8 g, 24 mmol) was added. The reaction mixture was allowed to react at 60° C. for 4 hours. After cooling, the polymer which was now insoluble in water, was separated and vacuum dried at room temperature overnight. The polymer was characterized by $^{13}C$ NMR, $^1H$ NMR, FTIR and GPC for each specific case and typically the allyl content was 50%.

EXAMPLE 13

Introduction of Cation Exchanging Groups

The poly(2-hydroxyethyl vinyl ether-co-2-allyloxyethyl vinyl ether) from example 12 was dissolved in 100 ml water/THF (1:1), treated with sodium hydrogen sulfite (13 g, 125 mmol) at pH=6 (45% NaOH(aq was used). The reaction mixture was allowed to react for 12 hours. The amount of sulfonate groups was determined by titration and was in accordance with the allyl groups present in the beginning of the reaction. The remaining hydroxyl groups were used in one typical example for the covalent coupling of the cation exchanger functionalized polymer to Sepharose HP beads.

Covalent Coupling of Poly(vinyl ethers) to a Hydrophilic Matrix

EXAMPLE 14

Coupling of poly(2-hydroxyethyl vinyl ether) (hydrophilic polymer)

23 g of poly(2-hydroxyethyl vinyl ether) from example 7 was; dissolved in 40 ml distilled water (solution 1).

Allyl-functionalized Sepharose® HP 40 g was suspended in 20 ml distilled water and 1.25 g of sodium acetate was added. The gel was activated with bromine until a slightly yellow colour stays. Sodium formate was added until the gel turns white again. This is solution 2.

The solutions were thermostated to a constant temperature of 30° C. and mixed and stirred for one hour. 5 g of NaOH and 0.1 g of $NaBH_4$ were added and after continuing stirring at 30° C. for 17 h, the solution was neutralized and the matrix was washed with water/ethanol/water.

EXAMPLE 15

Coupling of Cation Exchanger

The same conditions as in example 14 was applied to the coupling of the polymer from example 13 to epoxy-functionalized Sepharose HP.

EXAMPLE 16

Coupling of Anion Exchanger

The same conditions as in example 14 was applied to the coupling of the polymer from example 11 to epoxy-functionalized Sepharose HP.

Titration

In a typical procedure the anion exchanger matrix was suspended in 0.5M HCl and further saturated with 1 mM HCl. Next, 1 ml gel matrix was transferred to a titration vessel by using a small amount of distilled water. After dilution to a convenient volume for the subsequent titration, "2 drops" of concentrated $HNO_3$ was added. This solution was titrated with $AgNO_3$. Typically the $Cl^-$ capacity was determined to 0.16 mmol/ml gel for the ion exchanger prepared in example 16.

Chromatographic Evaluation

Gel Filtration using poly(2-hydroxyethyl vinyl ether)

The product from example 14, i.e. poly(2-hydroxyethyl vinyl ether) covalently attached to a Sepharose® HP matrix, was compared with Superdex® 30 PG in a representative protein separation. The proteins were dissolved in the buffer solution and the gel filtration gave the $K_{av}$- values for bovine serum albumin (BSA), ribonuclease, aprotinin and vitamin B 12 respectively, as shown in table 1.

TABLE 1

$K_{av}$-values from a typical comparative gel filtration procedure.

| Protein | Mw | Sepharose® HP $K_{av}$ | Superdex® 30 PG $K_{av}$ | Sepharose® HP polymermodified $K_{av}$ |
|---|---|---|---|---|
| BSA | 67 000 | 0.661 | 0.026 | 0.035 |
| Ribonucleas | 13 600 | 0.795 | 0.156 | 0.204 |
| Aprotinin | 6500 | | 0.364 | 0.359 |
| Vitamin B12 | 1400 | | 0.708 | 0.768 |

It is clearly shown from this table that this new polymer is well suited for the preparation of gel filtration media.

Anion Exchange Chromatography

The product from example 16, i.e. anion exchange polymer of example 11 covalently attached to a Sepharose® HP matrix, was compared with Q Sepharose® HP in a representative protein separation. Proteins (transferrin, ovalbumin and β-lactoglobulin) were dissolved in a buffer solution and applied to columns packed with the matrixes. The two chromatograms showed closely related elution profiles for the mixture of proteins.

We claim:

1. A separation method, comprising the steps of:
   i. contacting an aqueous liquid that contains a dissolved substance that is to be enriched with a polymer under conditions allowing selective partition of said substance to said polymer, based on one or more properties of the substance and polymer selected from the group consisting of: size and shape, net charge, isoelectric point, hydrophobicity, metal binding, content of exposed thiol groups, and biospecific affinity, whereafter
   ii. said polymer or part thereof containing said substance is removed from said aqueous liquid, characterized in that said polymer is a poly(vinyl ether) comprising different or identical vinyl ether subunits of the structure (Formula 1)

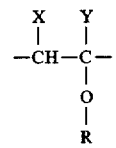

where

X and Y are selected among hydrogen and methyl; and

R is an organic group with a carbon atom attached directly to the oxygen atom, wherein the R substituent of more than one of the vinyl ether subunits is a hydrophilic organic group comprising at least one hydroxy and/or primary amino group ($H_2N$—) with a molar ratio (O+N)/C that is greater than 0.5.

2. The method according to claim 1, characterized in that the R substituents are selected among
   (a) hydrophobic groups, and
   (b) R'—B— where B is a hydrophilic organic bridge and R' is a substituted or unsubstituted OH group, or $NH_2$ group wherein said substituent is an organic residue R".

3. The method according to claim 2, characterized in that at least one of the vinyl ether subunits carries the organic residue R" and that this residue is selected among:
   a. groups comprising affinity ligands;
   b. groups comprising a thiol function (SH) or a function that quantitatively forms a disulphide with a thiol function; and
   c. hydrophilic organic groups.

4. The method according to claim 3, characterized in that at least one of the vinyl ether subunits carries an affinity ligand selected among:
   a. bioaffinity ligands;
   b. ion exchange groups;
   c. hydrophobic groups; and
   d. chelate groups comprising a chelated metal ion.

5. The method according to claim 2, characterized in that at least some R substituents are R'—B and that the hydrophilic organic bridge B consists of an unbroken straight, branched or cyclic carbon chain of $sp^3$-hybridized carbons, or a broken straight, branched or cyclic carbon chain of $sp^3$-hybridized carbon atoms wherein said chain is broken at one or more positions by an oxygen or a nitrogen atom.

6. The method of claim 5 wherein said organic bridge further comprises at least one hydroxy group and/or at least one primary amino ($NH_2$) group bound directly to one of said $sp^3$-hybridized carbon atoms, wherein
   (a) there is at most one oxygen or nitrogen atom bound to one and the same carbon atom in the chain, and
   (b) the molar ratio (O+N)/C in B is greater than or equal to 0.5.

7. The method according to claim 2, characterized in that the hydrophilic organic bridge B complies with the formula $[(CH_2)_n—O]_m$ wherein n is an integer that is 2, 3 or 4, and m is an integer that is 1–10.

8. The method of claim 7, wherein n is 2 and m is 1.

9. The method according to claim 2, characterized in that the poly(vinyl ether) is insoluble in the aqueous liquid by way of at least one of:

a. containing R constituents with R being R'—B, R' being a substituted OH or NH$_2$ group and at least one of said organic residues R" being covalently attached to a support or matrix carrier that is insoluble in the aqueous liquid;

b. containing R constituents with R being R'—B, R' being a substituted OH or NH$_2$ group and a plurality of said organic residues R" participating in inter- and/or intramolecular crosslinking of the poly(vinyl ether); or c. more than one said R substituents comprising hydrophobic groups that are physically adsorbed to a hydrophobic support or matrix carrier.

10. The method according to claim 1, characterized in that the poly(vinyl ether) has more than 10 subunits complying with formula 1 consecutively linked to each other.

11. The method according to claim 1 characterized in that a plurality of R substituents in the vinyl ether subunits carry a hydrophobic group that is selected among:

straight, branched or cyclic hydrocarbyl groups.

12. The method of claim 11, wherein said hydrophobic groups have 1–25 carbon atoms.

13. The method of claim 1, wherein said plurality of said vinyl ether subunits is at least 5% of said vinyl ether subunits.

14. The method of claim 1, wherein said R substituents comprise hydrophobic groups which are hydrocarbyl groups.

15. The method of claim 1 wherein X and Y are both hydrogen.

16. The method of claim 1 wherein the hydrophilic organic group of the R substituent of more than one of the vinyl ether subunits further comprises one or more groups selected from the group consisting of an ether group (—O—), a secondary amino group and a tertiary amino group.

17. The method of claim 1 wherein at least 5% of the R subunits of the vinyl ether subunits are hydrophilic organic groups comprising at least one hydroxy and/or primary amino group.

18. The method of claim 1 wherein at least 25% of the R substituents of the vinyl ether subunits are hydrophilic organic groups comprising at least one hydroxy and/or primary amino group.

* * * * *